US008703166B1

(12) United States Patent
Flynn

(10) Patent No.: US 8,703,166 B1
(45) Date of Patent: Apr. 22, 2014

(54) SYSTEMS AND METHODS FOR REDUCING MICROBIAL GROWTH

(76) Inventor: John Flynn, Burnsville, MN (US)

(*) Notice: Subject to any disclaimer, the term of this patent is extended or adjusted under 35 U.S.C. 154(b) by 99 days.

(21) Appl. No.: 13/010,584

(22) Filed: Jan. 20, 2011

(51) Int. Cl.
*A01N 25/12* (2006.01)
(52) U.S. Cl.
USPC ...... 424/409; 106/1.26; 106/1.29; 106/15.05; 106/18.36; 424/405; 424/411; 424/630; 424/639; 424/641; 424/646; 424/650; 424/682; 524/439

(58) Field of Classification Search
None
See application file for complete search history.

(56) References Cited

U.S. PATENT DOCUMENTS

| | | | |
|---|---|---|---|
| 3,197,313 A | 7/1965 | Greiner et al. | |
| 3,479,130 A | 11/1969 | Rapaport et al. | |
| 3,484,267 A | 12/1969 | Sadler, III | |
| 3,494,727 A | 2/1970 | Kapaport et al. | |
| 3,507,676 A | 4/1970 | McMahon et al. | |
| 3,528,842 A | 6/1970 | Skadulis et al. | |
| 3,598,627 A | 8/1971 | Klimboif et al. | |
| 3,884,706 A | 5/1975 | Little | |
| 3,992,146 A | 11/1976 | Fazzalari | |
| 4,088,810 A | 5/1978 | Lodge | |
| 5,216,864 A | 6/1993 | Urgero | |
| 5,382,475 A | 1/1995 | Mayser | |
| 5,415,919 A | 5/1995 | George et al. | |
| 5,427,793 A | 6/1995 | Bigham et al. | |
| 5,510,109 A * | 4/1996 | Tomioka et al. | 424/421 |
| 5,573,810 A | 11/1996 | Grubka | |
| 6,214,466 B1 | 4/2001 | Joedicke | |
| 6,245,381 B1 | 6/2001 | Israel | |
| 6,569,520 B1 | 5/2003 | Jacobs | |
| 6,585,813 B2 | 7/2003 | Kiik et al. | |
| 6,649,567 B2 | 11/2003 | Woods | |
| 6,719,987 B2 * | 4/2004 | Burrell et al. | 424/405 |
| 6,838,152 B2 | 1/2005 | Joedicke | |
| 7,060,658 B2 | 6/2006 | Joedicke | |
| 7,323,237 B2 | 1/2008 | Koschitzky | |
| 7,354,596 B1 | 4/2008 | Banovetz et al. | |
| 7,595,107 B2 | 9/2009 | Kalkanoglu et al. | |
| 7,687,106 B2 | 3/2010 | Hong et al. | |
| 7,788,870 B1 | 9/2010 | Spencer | |
| 2006/0188580 A1 * | 8/2006 | Sacks | 424/489 |

OTHER PUBLICATIONS

Label—Scotchgard Algae Resistant Roofing—by 3M, date available prior Jan. 20, 2011.*
Label—Zinc Shield—3M, date available prior to Jan. 20, 2011.*
Scotchgard (TM) Algae Resistant Roofing System, produced by 3M Corporation. (See attachment.) Wayback machine indicates a first-published date of Jan. 17, 2011.
Liquid Zinc (TM), produced by Great States Products, Lancaster, SC, 29721. (See attachment.) Wayback machine indicates a first-published date of May 25, 2005.

* cited by examiner

*Primary Examiner* — Neil Levy
(74) *Attorney, Agent, or Firm* — Underwood & Associates, LLC

(57) ABSTRACT

Antimicrobial and algaecidal products are disclosed. In general, the antimicrobial or algaecidal products can be adhered to structural components of buildings and include particles that, when combined with water, produce a solution that is toxic to organisms such as algae. The products provide an algaecidal wash as water percolates on, or through the product, and can prevent or control growth of unsightly algae and other microbes.

14 Claims, 4 Drawing Sheets

SYSTEMS AND METHODS FOR REDUCING MICROBIAL GROWTH

TECHNICAL FIELD

This disclosure relates to systems and methods for reducing microbial growth, in particular, algae growth on exterior portions of buildings and similar structures.

BACKGROUND

Algae and other microbial growth can be found in, and on structural members of buildings, including ceilings, floors, interior and exterior walls, and roofs, among other locations. Although algae growth does not typically threaten the structural integrity of building members, it can be unsightly. Removing algae and other microbes from buildings can be costly, and, if the problem is not resolved, can lower property values. Algae outbreaks can be seen in some building materials as dark stains and blotches; this can give the structure a deteriorated look, even though in most cases the algae is present predominantly on the surface of the material. The blue-green algae *Gloeocapsa magma* is a common microbe that can be found on roofs and exterior walls of buildings. Structural infestation by this algae is extensive in warm and humid climates, but is also commonplace in moderate-temperature, cooler areas. Infestations on roofs and walls are typically noticed first as dark spots, and then develop into long dark streaks as the algae reproduce and are carried by rain waters across the surface.

SUMMARY

In general, systems and methods for reducing, eliminating, or controlling microbial growth are disclosed. In particular, an algaecide product is disclosed that can be applied to a surface, where moisture that flows over the product becomes algaecidal upon contact and has the effect of reducing or eliminating algae or other microbial growth on the surface.

In one general aspect, this disclosure relates to the prevention of algae and other microbial growth and subsequent staining on interior and exterior surfaces. In one embodiment, metal particles are embedded within an adhesive strip; metallic ions are formed as moisture flows across the metal particles exposed on the strip and alters the surface so as to be toxic to algae.

In one general aspect, a composition for treating or preventing microbial growth is disclosed. The composition includes a pliable base matrix that itself includes a plurality of particles that, when exposed to moisture, produces a microbially toxic solution. The composition is capable of being attached to a surface.

In one embodiment, the pliable base matrix is one or more of: caulk, sealant, glue, putty, adhesive, binder, grout, gum, mud, paste, plaster, rubber, and solder.

In one embodiment, the microbe is algae, and in one embodiment the algae is *Gloeocapsa magma*.

In one embodiment, the microbially toxic solution includes the particles, or ions of the particles.

In one embodiment, the particles or ions of the particles are toxic to microbes through mutagenic processes or by inflicting damage to the cell wall of the microbe.

In one embodiment, the microbially toxic solution has a pH capable of reducing or eliminating the microbial growth.

In one embodiment, the plurality of particles includes one or more particles of: aluminum, iron, manganese, zinc, tin, lead, copper, boron, or quaternary ammonium salts.

In one embodiment, the pliable base matrix is an adhesive tape, and in some embodiments the adhesive tape is a foam tape.

In another general aspect, an algaecidal strip is disclosed. The algaecidal strip includes a flexible, adhesive base matrix that itself includes metal, metalloid, metal alloy, or semiconductor particles dispersed therein. The algaecidal strip further includes one or more channels that allow water to flow through a portion of the base matrix; wherein the water is converted to an algaecidal solution upon passing through the one or more channels or over the surface of the base matrix.

In one embodiment, the base matrix is an adhesive tape, and in some embodiments the adhesive tape is a foam tape.

In one embodiment, the algaecidal strip further includes a protective strip on one or more sides of the base matrix for protecting the particles from exposure to water.

In one embodiment, the particles are particles of one or more of aluminum, iron, manganese, zinc, tin, lead, copper, boron, or quaternary ammonium salts.

In one embodiment, the particles are in the form of granules, flakes, powders, shards, burrs, or chips.

In one general aspect, a method for controlling algae growth is disclosed. The method includes placing the composition of an above-described compound on a surface, wherein the surface is exposed to a source of water, and wherein the composition is configured to allow water to travel over, or percolate through the composition. In doing so, the water forms an algaecidal solution, wherein the algaecidal solution is allowed travel to a portion of the surface containing algae growth.

In one embodiment, the method further includes providing a water source in proximity to the composition to provide an algaecidal solution to the surface in the absence of rain.

In one embodiment, the surface is an exterior surface of a building structural or decorative component. In multiple embodiments, the surface is the surface of a roof, shingle, interior or exterior wall, floor, deck, joist, rafter, truss, stud, pier, window frame, window sill, masonry, concrete or wooden foundation member, veneer, stucco, insulation material, facade, fascia, trim, signage, sculpture, or framing member.

Certain advantages of the systems and methods include the capability to apply a microbial or algaecidal product to buildings and sculptures that is aesthetically pleasing. Another advantage, of many, is that surfaces can be kept clean and stain-free using a low maintenance system as described herein. Common methods to clean surfaces involve chemical treatments, power washing, and physical scrubbing, sandblasting and steaming. In addition to the associated costs, these methods can have other drawbacks. For example, active ingredients in chemicals may damage adjacent plant life. In addition, physical removal of the algae may cause premature wearing of the surface. If these maintenance items are not adequate or preferred, painting and premature replacement of materials may be required. These remedial options are costly, labor-intensive, and may not provide a lasting solution. Finally, user safety can becomes a concern when washing exterior surfaces due to working at sometimes dangerous heights.

The following references are incorporated by reference herein: U.S. Pat. No. 3,484,267 to Sadler disclosed a metallic flashing flange to be installed at the peak of shingle roofs to retard algae growth; U.S. Pat. No. 3,494,727 to Rapaport disclosed a metallic granule in asphalt shingles; U.S. Pat. No. 3,507,676 to McMahon discloses using zinc granules in roofing granules; U.S. Pat. No. 3,528,842 to Skadulis discloses using copper as algaecidal granules.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, and in which.

DETAILED DESCRIPTION OF ILLUSTRATIVE EMBODIMENTS

Figure 1:
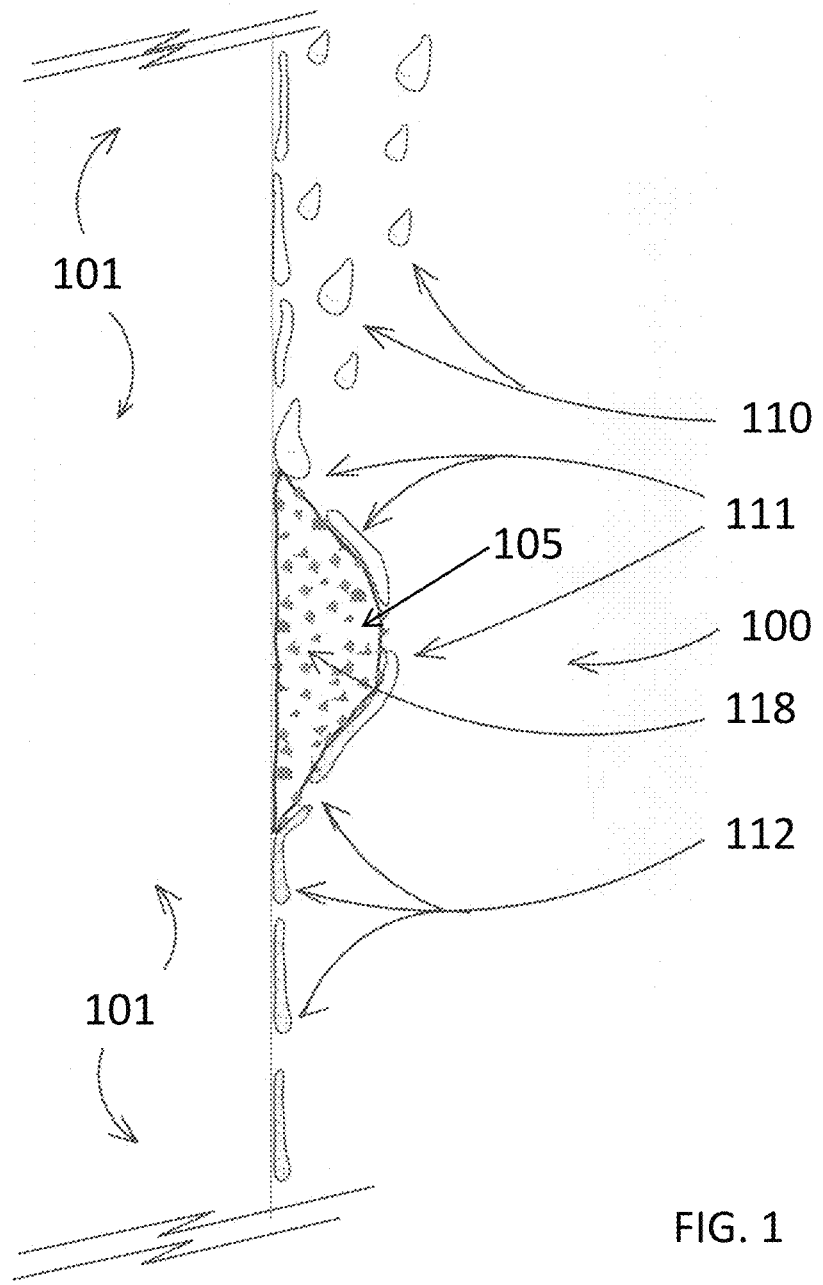
FIG. 1 is an antimicrobial strip, according to one embodiment.

In general, systems, methods, and articles of manufacture are disclosed that can be used to reduce the likelihood of microbial growth, particularly on exterior surfaces of buildings, sculptures, and other structures. In general, building structural components refers to structural components of any type of building, including, but not limited to: roofs, shingles, interior and exterior walls, floors, decks and decking, joists, rafters, trusses, studs, piers, window frames and window sills, masonry, concrete and wood foundation members, veneers, stucco, insulation materials, facades, sloped roofing, fascia and trim, signage, sculpture, bridges, walls, and any framing member. The term "building" carries its ordinary meaning in the art, and includes, but is not limited to: residential homes, apartments, and condominiums, barns, sheds, protective coverings for boats, recreational vehicles, and similar equipment, and commercial structures, such as restaurants, office buildings, warehouses, industrial complexes, malls, and other structures.

In general, reference to "microbe," "algae," or "algae growth" herein shall include and imply other forms of microbial growth, including, but not limited to mold, fungus, bacteria, moss and the like. It will also be understood herein the term 'surface' shall be a general description of areas that are capable of supporting algae growth.

Algae stains on buildings are known to be caused by at least three sources: the algae itself, residue left from algae, and trace amounts of dirt attached to the biofilm skin of the organism. Atmospheric factors such as temperature, humidity, precipitation, wind, sunlight, and others can affect growth rates. In addition, certain characteristics of the substrate supporting algae growth can affect the extent of the infestation, such as the material's density, porosity, pH and slope, among others. Usually, the worst staining tends to occur in surface locations that retain moisture or dry slowly. North- or east-facing sides of buildings, shingled and sloped roofs, shaded walls, areas below window sills and other locations of extended periods of dripping water can be particularly problematic for microbial infestation.

Algae stains can appear as uneven streaks and blotches when the substrate supporting growth is inhomogeneous, e.g., when density, porosity, pH, slope, sun and wind exposure, etc. vary across its surface. In some cases, algae can spread across large areas of a surface and even extend to adjoining structures (e.g., a neighboring house) by wind, which can make eradicating an infestation particularly difficult. Likewise, some algae strains can survive through cold, winter months, which can lead to recurring infestations.

One particularly prevalent area for algae stains to occur is on asphalt-shingle roofs. The rough granular surface of the shingles can provide a damp, porous surface, at least partially protected from direct sunlight. In light-colored shingles, the base material for the granules is commonly light-colored limestone, which provides calcium—a mineral source for algae that can allow it to flourish. Even on dark-colored shingles, limestone is sometimes used as fire-resistant filler. Algae can also grow on bare limestone within masonry, which is frequently used as a building material for its clean, white appearance and ability to be formed to a preferred shape.

Referring now to FIG. 1, a side-view of a strip of algaecidal compound 100 ("compound") is shown. The compound 100 is shown adhered to an exterior portion of a wall 101; however, the compound can be adhered to any building material substrate, including any of the building structural components referred to above. The compound 100 includes a pliable base matrix 105 having particles 118 embedded therein and on the surface of the matrix 105. Exemplary pliable base matrix materials include, without limitation: caulks, sealants, glues, putties, adhesives, binders, grout, gums, muds, pastes, plaster, rubber, e.g., rubber cement, and solder. Exemplary particles 118 in this and other embodiments include, without limitation, any metal, metalloid, metal alloy, semiconductor, inorganic or organic particle, or combinations thereof, having microbial toxicity by itself, or capable of producing a solution that is toxic to microbes when combined with a solvent such as water. Preferred particle materials include aluminum, iron, manganese, zinc, tin, lead, or copper, boron, salts, including quaternary ammonium salts and so-called "polyquats," although other materials known in the art to produce an antimicrobial or algaecidal effect may be substituted.

FIG. 1 shows droplets of rainwater 110 falling on, and running over the algaecidal compound 100. As the rainwater 110 runs across—and in some embodiments, through—the surface of the compound 100, particles 118 and, in some embodiments, ions of particles 118 leach into the rainwater, forming a solution (shown as droplets 111 in FIG. 1) that can be toxic to microbes, especially algae. In some embodiments, the porosity of the base matrix 105 can be chosen to retain water within the compound 100 for a preferred amount of time to control the resulting concentration of particles 118 and particle 118 ions in the solution (i.e., droplets 112 in FIG. 1). The porosity of the base matrix 105 can be controlled, among other methods, through selection of the pliable material, or by creating channels through the base matrix 105. Channels can be created through the compound 100 by methods known in the art, e.g., micro-machining, laser processing, and other methods.

In this and other embodiments, the algaecidal compound 100 can be formed by mixing particles 118 in a base matrix 105 in sufficient concentration to produce an antimicrobial or algaecidal solution as water runs across its surface. For example, still referring to FIG. 1, pure (i.e., non-toxic) water droplets 110 approach the compound 100; as the droplets traverse the compound 100 (shown as droplets 111) they begin to pick up particles and particle ions through leaching or solvation processes; the droplets continue to migrate across the surface of the compound 100 and emerge having microbial or algaecidal toxicity (droplets 112 in FIG. 1). The particles, e.g., particles 118 can be in the form of granules, flakes, powders, shards, burrs, chips, and the like. In some embodiments it can be preferable to use particles of extremely small size, e.g., micro- or nanoparticles, to maximize the surface-to-volume ratio of the particle. In some embodiments the particles can be affixed to an exterior surface of the base matrix only, so that the integrity of the base matrix itself is not compromised.

The algaecidal compound 100 can be made by mixing metallic particles within an uncured caulking material and applying the product to the surface as one would apply caulk or joint sealant. In one embodiment, the algaecidal compound 100 can be packaged within a typical caulking cartridge and applied to a surface with a caulk-gun application or similar method.

Figure 2:
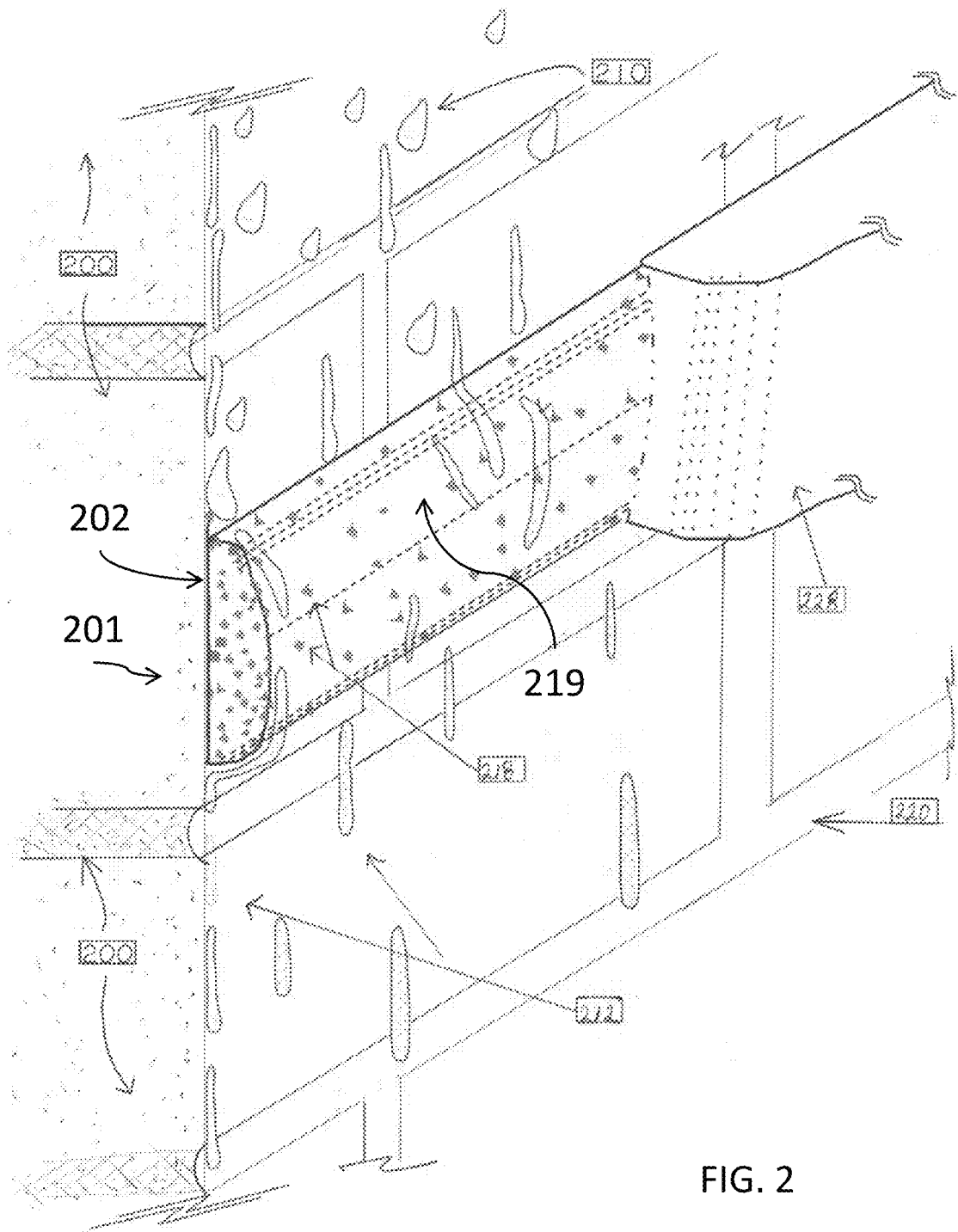
FIG. 2 is an antimicrobial strip, according to one embodiment.

Referring now to FIG. 2, a surface-mountable algaecidal strip ("strip") 201 is shown. The strip 201 has a substantially flat adhesive surface 202 configured hold the strip 201 to a wall 200 or other surface. Similar to the embodiment of FIG. 1, the strip 201 can include particles 218 embedded on an exterior surface of, and within a host matrix 219. The host matrix 219 in this embodiment can be a pliable putty or caulk material; in some embodiments, however, the host matrix 219 can be substantially rigid. The particles 218 are substantially similar to that described with respect to FIG. 1, in that they can cause a solution such as water to become algaecidal when the solution passes through, or over the strip 201.

Strip 201 can be mounted, for example, on an exterior surface of a building, such as a roof (e.g., the apex of a roof, or roof shingles) or wall, or other structure such as a sculpture, where it can come into contact with a source of water that flows over the strip 201 and thereby produce an antimicrobial or algaecidal solution as previously described. FIG. 2 shows the strip 201 mounted on an exterior portion of a concrete wall 200. Rain or other sources of moisture 210 can travel down the wall until it meets the strip 201. Here, the moisture 210 can travel over or through the strip 201, to produce the antimicrobial or algaecidal solution that washes the portions of the wall 200 below the strip 201 (e.g. wall portion 212 in FIG. 2). Such portions can include interior and exterior portions of the wall 200.

The embodiment of FIG. 2 also includes a peel-away protective layer 228. The protective layer 228 can be a paper product, such as a wax paper product, that protects the strip before it is used in a manner described herein. A protective layer can be beneficial particularly in geographical regions having high humidity or where moisture would otherwise be capable of reaching the particles 218 on, or within the strip 201 before its intended use.

One method of reducing the likelihood of algae growth on an exterior wall includes the steps of: adhering the algaecidal strip 201 to a surface of a wall 200 where it is likely to receive moisture 210; removing the protective layer 228, and allowing the moisture 210 to wash over, and, in some embodiments, through the strip 201 to produce an algaecidal solution. The algaecidal solution then travels beyond the strip 201, e.g., down, as shown in FIG. 2, encountering any algae that may be growing on the wall 200, e.g., on wall regions 212. One advantage of a strip 201 algaecidal product as described in FIG. 2 is the ability to apply the product to a surface, such as an exterior wall, without the mess that is often created when applying caulks and the like to surfaces.

In these and other embodiments, the strip 201 can be configured in any orientation, dimension, or shape to maximize its antimicrobial or algaecidal effectiveness against such organism growth. For example, while the strip 201 in FIG. 2 is shown having a semi-spherical cross-section that allows moisture to easily pass over it, the strip 201 can optionally include grooves, channels, or coves that substantially retain water; small channels in the strip 201 can allow retained moisture to slowly percolate therethrough, which, as described above, can affect the toxicity of the algaecidal solution.

Figure 3:
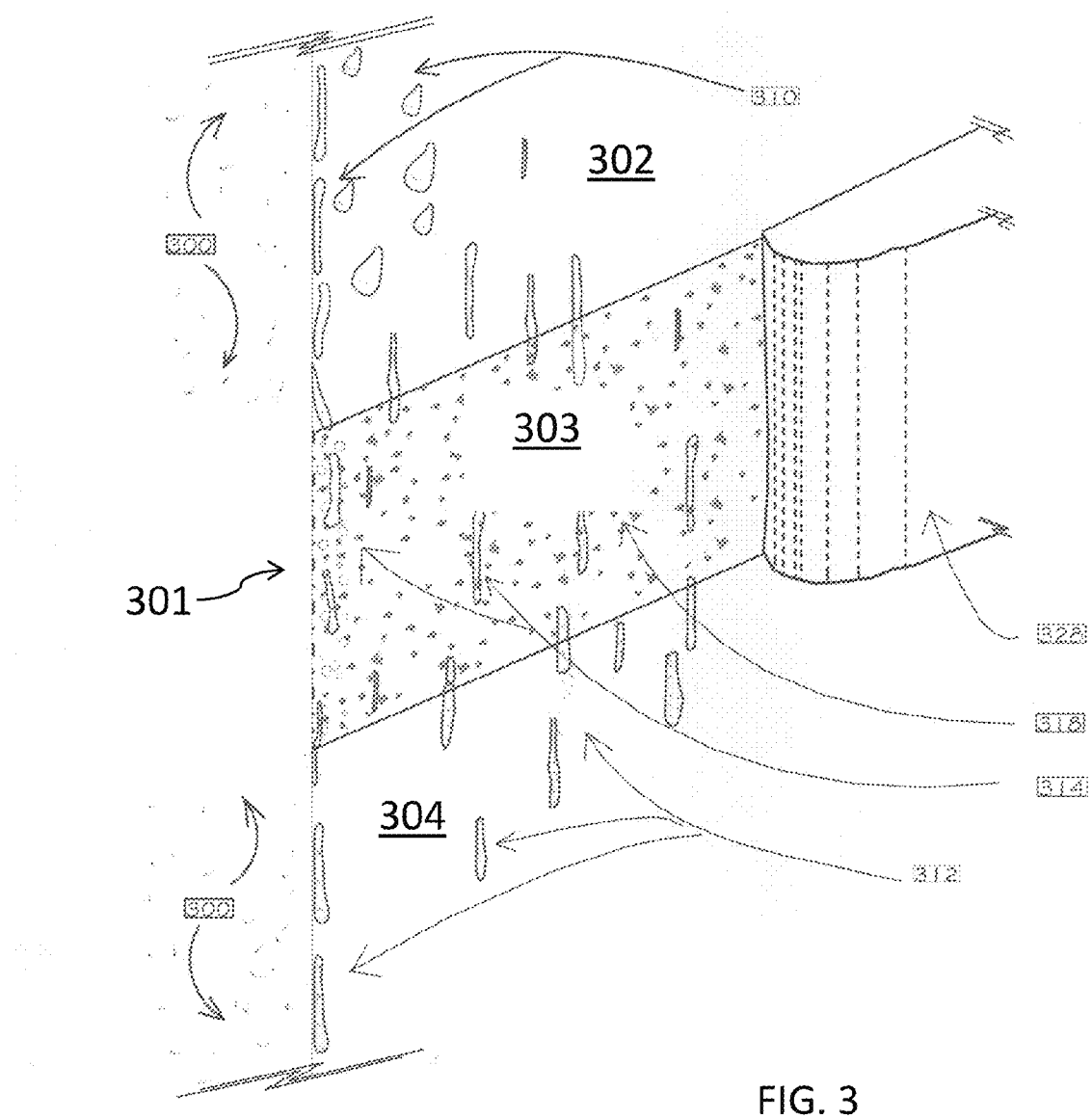
FIG. 3 is an antimicrobial strip, according to one embodiment.

Referring now to FIG. 3, an antimicrobial tape 301 is shown. The antimicrobial tape 301 includes an adhesive tape substrate ("substrate") 303 capable of adhering to a wall 300 or other structures, including, but not limited to: masonry, brick, wood, shingles, fiberglass, granite, and other building materials as previously described. Particles 318 of the type described heretofore, which are capable of producing an antimicrobial solution when exposed to moisture, are present on, and within the substrate 303. Similar to the embodiment described with respect to FIG. 2, the tape 301 includes a peel-away protective layer 328 that can be removed once the tape 301 has been applied to the surface intended for use.

Similar to the embodiments described above, FIG. 3 shows moisture droplets 310 from above the tape (the area labeled 302) being drawn down by gravity, across the surface of the tape 301, and emerging on the downward side (the area labeled 304) as droplets of antimicrobial solution 312. Thus, the area of the wall 300 below the tape 301, i.e., area 304 can be washed by the droplets of antimicrobial solution 312 over an extended period of time, and thus reduce the likelihood of algae or other microbial growth in these areas.

In this and other embodiments, the size of the antimicrobial or algaecidal product can be chosen to best suit the intended application. For example, in this embodiment, the tape can be any thickness, size, or length to provide optimal antimicrobial effectiveness across a given surface. Similarly, the antimicrobial or algaecidal product can be adhered by means known in the art, such as stapling, nailing, gluing, tacking, and similar methods; the product can also be held in place using external hardware, including, but not limited to: brackets, pipe clamps, and the like.

Figure 4:
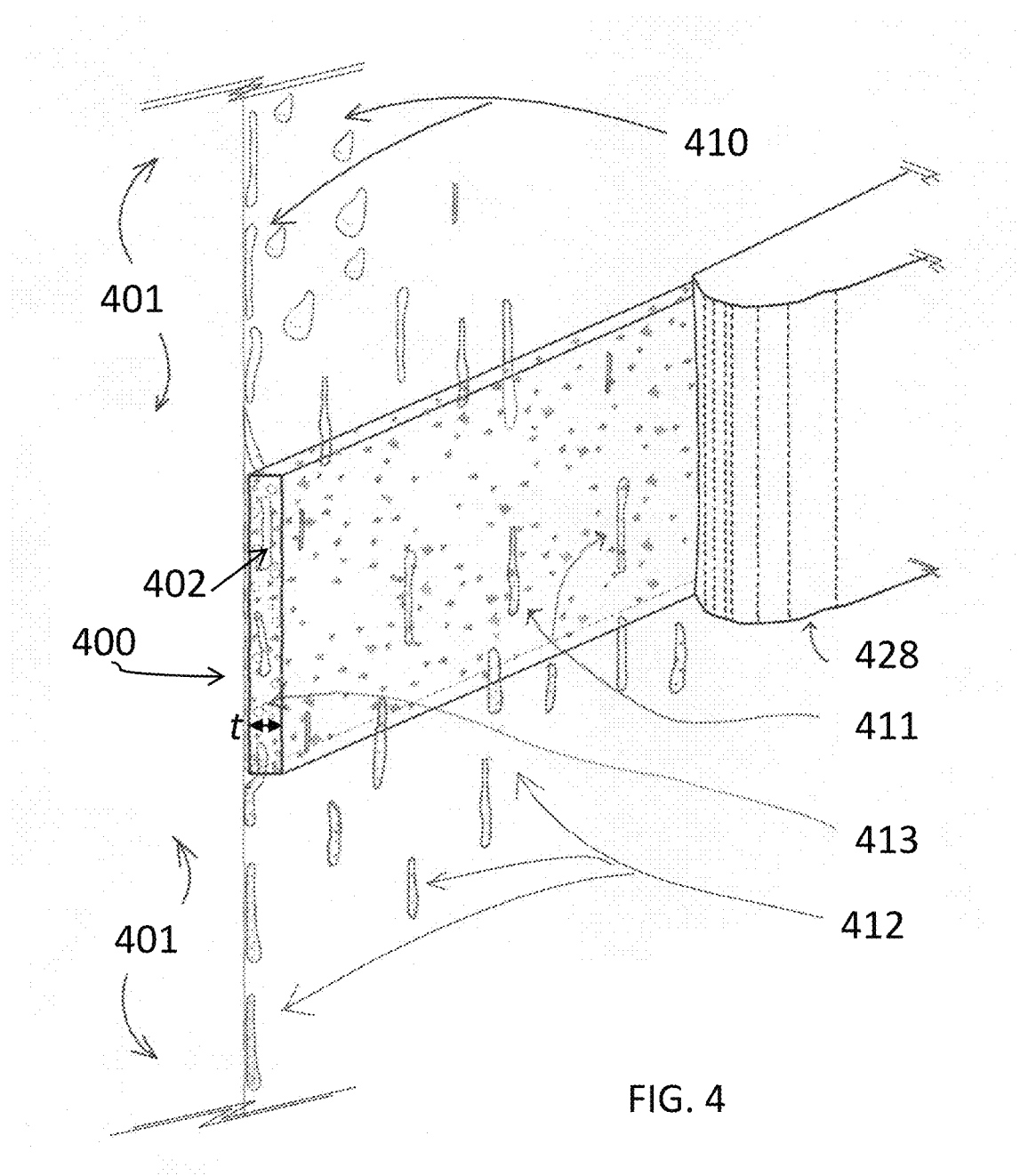
FIG. 4 is an antimicrobial strip, according to one embodiment.

Referring now to FIG. 4, one embodiment of an antimicrobial tape 400 is shown. In this embodiment, the tape 400 has a thickness t as shown that allows moisture 410 to percolate through the tape 400. Similar to the embodiments described above, the tape 400 in FIG. 4 is shown applied to a surface which, in this example, is an exterior building wall 401. The tape 400 can be porous to allow moisture from rainwater and the like (e.g. droplets 410) to percolate through (e.g., droplet 402) and over (e.g., droplets 411) the tape and extract particles 413 and/or particle ions to form an antimicrobial solution as previously described herein. Upon exiting the tape 400, the antimicrobial solution (e.g., droplets 412) can "wash" the building wall 401 of algae and other microbes. The tape 400 also includes an optional peel-away protective layer 428 which has been described with respect to FIGS. 2 and 3.

Exemplary tapes for use in this embodiment include so-called "foam tapes," although other types of tape having a desired thickness and porosity may be substituted. Foam tapes generally have one side with an adhesive strip that can be used to mount the tape (e.g. tape 400) to a surface. In these cases, particles that, when combined with water, form an antimicrobial or algaecidal solution can be integrated within the foam portion of the tape, e.g., during manufacture. In some embodiments, foam tapes having double-sided adhesives can be used, where one side of the tape is used to adhere the tape to a surface such as a wall, and the other adhesive side can be used to hold the antimicrobial particles.

In all embodiments, aesthetic qualities of the antimicrobial or algaecidal particles can be chosen to blend with building design aspects, including, but not limited to: color, texture, style, shape, architecture, and the like. In some embodiments, especially those antimicrobial or algaecidal products having a thickness to allow moisture percolation (e.g., the embodiment of FIG. 4), one or more sides of the product can include veneers, textures, colors, and other elements that serve to blend the product into its architectural or aesthetic surroundings.

The antimicrobial or algaecidal embodiments described herein and equivalents can be placed on, adhered to, directly or indirectly, or incorporated into any building component.

In general, a method for controlling microbial growth, including algae growth on a surface includes applying an antimicrobial or algaecidal product as described herein, e.g., the embodiments of FIG. 1, 2, 3, or 4, at or near the surface site where microbial growth could occur or is occurring. Generally, the antimicrobial product can be placed in a location above the site where microbial growth is occurring or may occur, and, in general, the antimicrobial solution formed by the product can be pulled down by gravitational forces to wash an area underneath or downstream of the product. The antimicrobial products described can be placed preferably at the highest level on a given surface to maximize the exposure of the resultant antimicrobial solution to the surface below. In general, the antimicrobial and algaecidal products described herein can be used both to treat existing infections and prevent infections from occurring.

A number of illustrative embodiments have been described. Nevertheless, it will be understood that various modifications may be made without departing from the spirit and scope of the various embodiments presented herein. For example, the antimicrobial or algaecidal solution can be toxic via mutagenic processes, destruction or compromise of the organisms' cell wall(s), or by forming a solution having a toxic pH (e.g., acidic or basic so as reduce the likelihood of sustaining microbial life). The above description of exemplary embodiments refers to rainwater as the moisture source that is ultimately converted to the antimicrobial or algaecidal solution. However, it will be understood that any source of water or other preferred liquid can be plumbed to a location proximal to the antimicrobial or algaecidal compounds, strips, and the like. In this manner, regular washings of walls, e.g., exterior walls, can occur using timers that automatically supply water, e.g., in the form of a mist or trickle at regular intervals. While the exemplary embodiments of FIGS. 1-4 show exterior walls on which the antimicrobial or algaecidal products are applied, the products can be applied to interior walls and surfaces where algae growth can occur, such as bathrooms, crawlspaces, attics, e.g., the underside of roof decking, and any other structure. Accordingly, other embodiments are within the scope of the following claims.

What is claimed is:

1. A composition for reducing the likelihood of microbial growth, comprising:
a plurality of uncomplexed, elemental metal particles disposed in an adherent, pliant, and flowable base matrix, such that said composition is capable of producing an antimicrobial solution when exposed to moisture and capable of being attached to a surface of a structural component in a desired molded form;
wherein said base matrix is a caulk or a putty or a combination thereof; and
wherein said plurality of uncomplexed, elemental metal particles comprises uncomplexed, elemental particles of aluminum, iron, manganese, zinc, tin, lead, copper, boron, or any combination thereof.

2. The composition of claim 1, wherein said microbial growth is growth of algae.

3. The composition of claim 2, wherein said algae is *Gloeocapsa magma*.

4. The composition of claim 1, wherein said antimicrobial solution comprises ions of said elemental particles, or a dispersion of said uncomplexed, elemental metal particles, or a combination thereof.

5. The composition of claim 1, wherein said antimicrobial solution has a pH that is sufficiently toxic to reduce the likelihood of, or substantially prevent said microbial growth.

6. A method for controlling algae growth, comprising:
applying an algaecidal composition to the surface of a structural component, the algaecidal composition comprising:
a plurality of uncomplexed, elemental metal particles disposed in an adherent, pliant, and flowable base matrix, such that said composition is capable of producing an antimicrobial solution when exposed to moisture and capable of being attached to a surface of a structural component in a desired molded form;
wherein said base matrix is a caulk or a putty or a combination thereof; and
wherein said plurality of uncomplexed, elemental metal particles comprises uncomplexed, elemental particles of aluminum, iron, manganese, zinc, tin, lead, copper, boron, or any combination thereof;
wherein said surface is exposed to a water source;
wherein said composition is configured to allow said water to travel over, or percolate through said composition to form an algaecidal solution and
placed such that said algaecidal solution is capable of flowing to a portion of said surface harboring algae growth.

7. The method of claim 6, wherein said structural component is an exterior surface of a building structural or decorative component.

8. The method of claim 6, wherein said structural component is a roof, shingle, interior or exterior wall, floor, deck, joist, rafter, truss, stud, pier, window frame, window sill, masonry member, concrete or wooden foundation member, veneer surface, stucco surface, insulation material, façade surface, fascia surface, trim surface, signage member, sculpture, or framing member.

9. The method of claim 6, further comprising providing said water source in proximity to said composition to provide an algaecidal solution to said surface when desired.

10. The composition of claim 1, wherein said base matrix comprises channels for channeling said moisture therethrough.

11. The composition of claim 1, wherein said elemental metal particles are microparticles or nanoparticles.

12. The composition of claim 1, wherein said elemental metal particles are affixed to the exterior surface of said base matrix.

13. The composition of claim 1, further comprising a colorant for blending said composition into its architectural or aesthetic surroundings.

14. A method for making a composition for reducing the likelihood of microbial growth, comprising:
mixing a plurality of uncomplexed, elemental metal particles into an adherent, pliant, and flowable base matrix, such that said composition is capable of producing an antimicrobial solution when exposed to moisture and capable of being attached to a surface of a structural component in a desired molded form;

wherein said base matrix is a caulk or a putty or a combination thereof; and wherein said plurality of uncomplexed, elemental metal particles comprises uncomplexed, elemental particles of aluminum, iron, manganese, zinc, tin, lead, copper, boron, or any combination thereof.

* * * * *